(12) United States Patent
Bae et al.

(10) Patent No.: US 9,993,217 B2
(45) Date of Patent: Jun. 12, 2018

(54) PRODUCING PANORAMIC RADIOGRAPH

(71) Applicants: VATECH Co., Ltd., Gyeonggi-do (KR); VATECH EWOO Holdings Co., Ltd., Gyeonggi-do (KR)

(72) Inventors: Woong Bae, Gyeonggi-do (KR); Sang Og Na, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 0 days. days.

(21) Appl. No.: 15/140,360

(22) Filed: Apr. 27, 2016

(65) Prior Publication Data

US 2016/0310097 A1    Oct. 27, 2016

(30) Foreign Application Priority Data

Apr. 27, 2015  (KR) ........................ 10-2015-0059069

(51) Int. Cl.
| | |
|---|---|
| *G06K 9/00* | (2006.01) |
| *A61B 6/14* | (2006.01) |
| *A61B 6/00* | (2006.01) |
| *A61B 6/03* | (2006.01) |
| *A61B 6/02* | (2006.01) |

(52) U.S. Cl.
CPC ............ *A61B 6/5205* (2013.01); *A61B 6/027* (2013.01); *A61B 6/032* (2013.01); *A61B 6/14* (2013.01); *A61B 6/5223* (2013.01)

(58) Field of Classification Search
CPC ..... A61B 6/5205; A61B 6/5223; A61B 6/027; A61B 6/032; A61B 6/14

USPC .............. 382/276, 128, 131, 132, 151, 154; 378/38–40, 4, 168, 190–191

See application file for complete search history.

(56) References Cited

U.S. PATENT DOCUMENTS 4,176,278 A * 11/1979 Cushman ............. A61B 6/0478
                                                    378/119
5,784,429 A    7/1998 Arai
(Continued)

FOREIGN PATENT DOCUMENTS

| EP | 2223653 A1 | 9/2010 |
|---|---|---|
| JP | 2008-086659 A | 4/2008 |

(Continued)

OTHER PUBLICATIONS

Pedro H. M. Lira et al., "Panoramic Dental X-Ray Image Segmentation and Feature Extraction", Proceedings of V Workshop of Computing Vision, Sao Paulo, Brazil, 2009, XP-002751412.

(Continued)

*Primary Examiner* — Sheela C Chawan
(74) *Attorney, Agent, or Firm* — IP Legal Services, LLC

(57) ABSTRACT

The disclosure is related an apparatus and method for producing a panoramic radiograph of a target object using a three dimensional (3D) radiograph of the same object. The apparatus may include a communication circuit and a processor. The communication circuit may be configured to receive 3D radiograph digital data of the 3D radiograph. The processor may be configured to generate a plurality of x-ray projection images of the target object by performing forward-projection on voxels associated with the target object, and to combine the generated x-ray projection images to produce the panoramic radiograph of the target object.

8 Claims, 7 Drawing Sheets

(56) References Cited

U.S. PATENT DOCUMENTS

| | | | |
|---|---|---|---|
| 7,397,890 B2* | 7/2008 | Sukovic | A61B 6/032 378/38 |
| 8,693,624 B2 | 4/2014 | Spartiotis et al. | |
| 9,269,168 B2* | 2/2016 | Inglese | A61B 6/4241 |
| 2006/0203959 A1 | 9/2006 | Spartiotis et al. | |
| 2008/0019477 A1 | 1/2008 | Spartiotis et al. | |
| 2008/0063139 A1 | 3/2008 | Pantsar et al. | |
| 2010/0142673 A1 | 6/2010 | Pantsar et al. | |
| 2010/0208866 A1 | 8/2010 | Spartiotis et al. | |
| 2010/0246761 A1 | 9/2010 | Pantsar et al. | |
| 2011/0044520 A1 | 2/2011 | Nakai et al. | |
| 2011/0103659 A1 | 5/2011 | Choi | |
| 2012/0039435 A1 | 2/2012 | Arai et al. | |
| 2012/0092334 A1 | 4/2012 | Yoo | |
| 2012/0224762 A1 | 9/2012 | Choi et al. | |
| 2013/0003921 A1 | 1/2013 | Spartiotis et al. | |
| 2013/0329854 A1 | 12/2013 | Spartiotis et al. | |
| 2015/0146853 A1 | 5/2015 | Spartiotis et al. | |
| 2015/0213633 A1* | 7/2015 | Chang | G01N 23/046 382/284 |

FOREIGN PATENT DOCUMENTS

| | | |
|---|---|---|
| JP | 2010-011910 A | 1/2010 |
| JP | 2010-148676 A | 7/2010 |
| JP | 2012-061016 A | 3/2012 |

OTHER PUBLICATIONS

K. Ogawa et al., "Development of a new dental panoramic radiographic system based on a tomosynthesis method", Dentomaxillofacial Radiology, vol. 39, No. 1, Jan. 1, 2010, pp. 47-53, XP055302062.

Europeal Patent Office, Office Action of EP Application No. 13 790 689.7, dated Sep. 23, 2016.

Korean Intellectual Property Office, International Search Report of International Application No. PCT/KR2013/004367, dated Aug. 6, 2013.

Korean Intellectual Property Office, Written Opinion of International Application No. PCT/KR2013/004367, dated Aug. 6, 2013.

* cited by examiner

PRODUCING PANORAMIC RADIOGRAPH

CROSS REFERENCE TO PRIOR APPLICATIONS

The present application claims priority under 35 U.S.C. § 119 to Korean Patent Application No. 10-2015-0059069 (filed on Apr. 27, 2015).

The subject matter of this application is related to U.S. patent application Ser. No. 14/401,726 filed Nov. 17, 2014, the teachings of which are incorporated herein their entirety by reference.

BACKGROUND

The present disclosure relates panoramic radiography and, more particularly, to producing a panoramic radiograph using a three-dimensional (3D) image.

A panoramic radiograph is a panoramic view of a two-dimensional (2D) x-ray dental arch image including a maxilla dental arch and a mandible dental arch. The panoramic radiograph may be referred to as a panoramic x-ray image. Such a panoramic radiograph shows the maxilla teeth and mandible teeth in a panoramic view. The panoramic radiograph is frequently used by professions in dental clinics for diagnosis of patient's dentition, such as teeth conditions and teeth arrangements.

A three-dimensional (3D) radiograph is also frequently used in dental clinics. The 3D radiograph may be referred to a 3D x-ray image. The 3D panoramic radiograph is used to examine a dentition for treatments requiring high precision, such as dental implant treatments. Such a 3D panoramic radiograph is a tomography produced by a specialized machine such as a 3D computed tomography device (CT), such as a dental 3D CT scanner.

As described, a panoramic x-ray image and a 3D x-ray image are frequently used in dental clinics in order to examine a patient's dentition. However, two separated machines are required to obtain the panoramic radiograph and the 3D radiograph.

SUMMARY

This summary is provided to introduce a selection of concepts in a simplified form that is further described below in the Detailed Description. This summary is not intended to identify key features or essential features of the claimed subject matter, nor is it intended to be used to limit the scope of the claimed subject matter.

Embodiments of the present disclosure overcome the above disadvantages and other disadvantages not described above. Also, embodiments of the present disclosure are not required to overcome the disadvantages described above, and embodiments of the present disclosure may not overcome any of the problems described above.

In accordance with an aspect of the present embodiment, a panoramic radiograph may be produced without using a panoramic radiography machine.

In accordance with another aspect of the present embodiment, a panoramic radiograph and a 3D radiograph may be produced using one machine.

In accordance with still another aspect of the present embodiment, a panoramic x-ray image may be produced by a 3D CT scanner.

In accordance with yet another aspect of the present embodiment, a panoramic radiograph may be produced using a 3D radiograph digital data generated by a 3D CT scanner.

In accordance with at least one embodiment, an apparatus may be provided for producing a panoramic radiograph of a target object using a three dimensional (3D) radiograph of the same object. The apparatus may include a communication circuit and a processor. The communication circuit may be configured to receive 3D radiograph digital data of the 3D radiograph. The processor may be configured to generate a plurality of x-ray projection images of the target object by performing forward-projection on voxels associated with the target object, and to combine the generated x-ray projection images to produce the panoramic radiograph of the target object.

The processor may be configured to detect a region of interest (ROI) including the target object in the 3D radiograph based on the received 3D radiograph digital data, to virtually locate a light receiving plane in front of the detected ROI and virtually locate a light source in back of the detected ROI, to determine voxels between the light source and each pixel of the light receiving plane, and to perform line integral on the determined voxels to generate the plurality of x-ray projection images.

The processor may further configured to use at least one of a morphology image processing (MIP) algorithm, an edge detection algorithm, and a blob detection algorithm to detect the ROI and to set at least one image layer in the detected ROI.

The processor may further configured to rotate the light receiving plane and the light source along the at least one image layer to generate the plurality of x-ray projection images.

The 3D radiograph of the same object may be generated by a 3D computerized tomography (CT) scanner which is separated from the apparatus.

In accordance with another embodiment, a method may be provided for producing a panoramic radiograph of a target object using a three dimensional (3D) radiograph of the same object. The method may include receiving 3D radiograph digital data of the 3D radiograph, generating a plurality of x-ray projection images of the target object by performing forward-projection on voxels associated with the target object based on the received 3D radiograph digital data, and combining the generated x-ray projection images to produce the panoramic radiograph of the target object.

BRIEF DESCRIPTION OF THE DRAWINGS

The above and/or other aspects of some embodiments of the present invention will become apparent and more readily appreciated from the following description of embodiments, taken in conjunction with the accompanying drawings, of which.

DETAILED DESCRIPTION OF EMBODIMENTS

Figure 1:
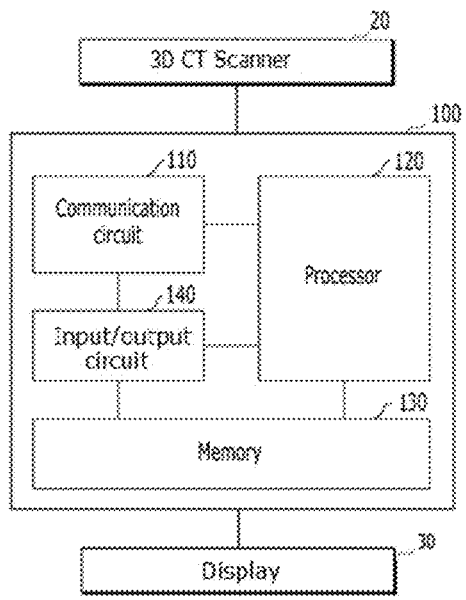
FIG. 1 illustrates a panoramic radiography producing apparatus in accordance with at least one embodiment of the present disclosure.

Reference will now be made in detail to exemplary embodiments of the present disclosure, examples of which are illustrated in the accompanying drawings, wherein like reference numerals refer to like elements throughout. The embodiments are described below, in order to explain embodiments of the present disclosure by referring to the figures.

In accordance with at least one embodiment, a dental panoramic radiograph may be produced using a dental three dimensional (3D) computerized tomography (CT) scanner, instead of using a panoramic radiography machine. In particular, a dental panoramic radiograph may be produced using a 3D radiograph of a patient's dental arch that is captured and produced by a dental 3D CT scanner. Such a dental panoramic radiograph may be produced by a panoramic radiograph producing apparatus in accordance with at least one embodiment. Hereinafter, the panoramic radiograph producing apparatus and a method for producing a panoramic radiograph in accordance with embodiments of the present disclosure will be described with reference to the accompanying drawings. For convenience and ease of understanding, embodiments of the present disclosure will be described as producing a dental panoramic radiograph. However, the embodiments of the present disclosure are not limited thereto. For example, the embodiments of the present disclosure may be applied to producing panoramic x-ray images of any type objects.

As described, the panoramic radiography producing apparatus may produce a panoramic radiograph using a 3D radiograph of a patient's dental arch. Hereinafter, a structure and a configuration of such a panoramic radiography producing apparatus will be described with reference to FIG. 1.

FIG. 1 illustrates a panoramic radiography producing apparatus in accordance with at least one embodiment of the present disclosure.

Referring to FIG. 1, panoramic radiograph producing apparatus 100 may obtain a 3D radiograph of a target object from other entities and produce a panoramic radiograph of the same object using digital information of the obtained 3D radiograph in accordance with at least one embodiment. The 3D radiograph of the target object may include digital information for producing a panoramic radiograph of the same target object. Such 3D radiograph digital information may be and voxel data of a 3D radiograph for expressing the target object in three dimensions.

Such panoramic radiograph producing apparatus 10 may be connected to 3D CT scanner 20 and display 30 in accordance with at least one embodiment. 3D CT scanner 20 may produce a 3D radiograph of a target object and provide the produced 3D radiograph to panoramic radiograph producing apparatus 100. Display 30 may receive a panoramic radiograph produced by panoramic radiograph producing apparatus 100 and display the received panoramic radiograph in response to an operator's control.

For example, 3D CT scanner 20 may be a typical 3D radiography machine such as a cone beam computed tomography (CBCT) and a computed tomography (CT). Display 30 may be a device for displaying a panoramic radiograph produced by panoramic radiograph producing apparatus 100. Display 30 may be various types of a display device, such as a liquid crystal display (LCD), a light emitting diode (LED) display, an active matrix organic light emitting diode (AMOLED) display, a cathode ray tube (CRT) display, and likes.

In FIG. 1, display 30 is illustrated as a device separated and independent from 3D CT scanner 20 and panoramic radiograph producing apparatus 100, but the embodiments of the present disclosure are not limited thereto. For example, such display 30 may be implemented within at least one of 3D CT scanner 20 and panoramic radiograph producing apparatus 100.

As shown in FIG. 1, panoramic radiograph producing apparatus 100 is illustrated as an independent single apparatus separated from 3D CT scanner 20 and display 30. However, embodiments of the present disclosure are not limited thereto. For example, panoramic radiography producing apparatus 100 may be implemented inside 3D CT scanner 20 with display 30, as single machine. For another example, panoramic radiograph producing apparatus 100 may be implemented as a circuit board attachable to or detachable from a predetermined slot in a circuit board. Such panoramic radiograph producing apparatus 10 may be inserted at a predetermined slot of a typical 3D CT scanner. In this case, panoramic radio graph producing apparatus 100 may use constituent elements (e.g., processors or memoires) of the typical 3D CT scanner for producing a panoramic radiograph. Furthermore, panoramic radiograph producing apparatus 10 may be implemented as a circuitry card with a predetermined communication interface such as a universal serial bus (USB) interface. Such panoramic radiograph producing apparatus 10 may be coupled with a typical 3D CT scanner through a USB slot. In this case, panoramic radio graph producing apparatus 10 may use constituent elements (e.g., processors or memoires) of the typical 3D CT scanner for producing a panoramic radiograph. Furthermore, panoramic radiograph producing apparatus 100 may be implemented as software program or application and installed in a typical 3D CT scanner. In this case, upon installing and execution of the predetermined software program, a typical 3D CT scanner might produce a panoramic radiograph by controlling constitute elements of the typical 3D CT scanner.

As another example, panoramic radiograph producing apparatus 10 may be located a comparatively long distance from 3D CT scanner 20. In this case, panoramic radiograph producing apparatus 100 may be connected to 3D CT scanner 20 through a communication network. As still another example, panoramic radiograph producing apparatus 100 may be not coupled to 3D CT scanner 20. In this case, panoramic radiograph producing apparatus 100 may obtain 3D radiograph i) by downloading from other entities coupled through a communication network, ii) from a secondary external memory coupled thereto through a predetermined interface, iii) inputted by an operator through an input circuit of panoramic radiograph producing apparatus 100. However, embodiments of the present disclosure are not limited thereto.

Hereinafter, such panoramic radiograph producing apparatus 100 will be described in more detail. As shown in FIG. 1, panoramic radiograph producing apparatus 100 may include communication circuit 110, processor (e.g., central processing unit) 120, memory 130, and input and output circuit 140 in accordance with at least one embodiment.

Communication circuit 110 may be a circuit for communicating with other entities coupled to panoramic radiograph producing apparatus 100. Such communication circuit 110 may enable panoramic radiograph producing apparatus 100 to communicate with other entities through a communication network. For example, communication circuit 110 may establish at least one of wireless and wired communication links to other entities (e.g., 3D CT scanner 20 and display 30) through a communication network or directly. Through the established communication links, the communication circuit 110 may receive information from or transmit information to 3D CT scanner 20 and display 30.

Furthermore, communication circuitry 110 transmits and receives signals to/from other entities through a communication network based on various types of communication schemes. Communication circuitry 110 may be referred to as a transceiver and include at least one of a mobile communication circuit, a wireless internet circuit, a near field communication (NFC) circuit, a global positioning signal receiving circuit, and so forth. Particularly, communication circuit 110 may include a short distance communication circuit for short distance communication, such as NFC, and a mobile communication circuit for long range communication through a mobile communication network, such as long term evolution (LTE) communication or wireless data communication (e.g., WiFi). In addition, communication circuit 110 may provide a communication interface between panoramic radiograph producing apparatus with other entities using various communication schemes.

Input/output circuit 140 may receive various types of signals from an operator for controlling apparatus 100 in accordance with at least one embodiment. Input circuitry 140 may include a keyboard, a keypad, a touch pad, a mouse, and likes. In addition, input circuitry 140 may be a graphic user interface capable of detecting a touch input.

Furthermore, Input/output circuitry 140 may provide an interface for receiving input information from other entities including an operator and providing information to other entities. Such input/output circuitry 140 may be realized to support in various types of standardized protocols and interface schemes.

Memory 130 may store various types of information, generated in apparatus 100 and received from other entities such as 3D CT scanner 20. Memory 130 may further store various types of applications and software programs for controlling constituent elements or performing operations associated with producing panoramic radiograph using 3D radiograph digital data.

In accordance with at least one embodiment, memory 130 may store intermediate image data (e.g., 2D x-ray projection image data) generated for producing a panoramic radiograph, resultant image data (e.g., the panoramic radiograph), information and variables necessary to perform operations for producing the panoramic radiograph. For example, memory 130 may store various types of image data, such as image data in a digital imaging and communications in medicine (DICOM) type, a BMP type, a JPEG type, and a TIFF type.

Memory 130 may further store software programs and a firmware. Memory 130 may include a flash memory, a hard disk, a multimedia card (MMC), a secure digital card, an extreme digital card, a random access memory (RAM), a static random access memory (SRAM), a read-only memory (ROM), an electrically erasable programmable read-only memory (EEPROM), a programmable read-only memory, a magnetic resistive random access memory, a magnetic disk, and an optical disk. However, the embodiments of the present disclosure are not limited thereto.

Processor 120 may control constituent elements of panoramic radiograph producing apparatus 100 and perform operations for producing a panoramic x-ray image of a target object using a 3D radiograph from other entities, such as 3D CT scanner 20. In addition, processor 120 may control constituent elements of other coupled devices, such as 3D photographing apparatus 20 and display 30, in cooperation with the coupled devices, and perform operations associated with the coupled devices in cooperation with the coupled devices.

Processor 120 may be referred to as a central processing unit (CPU). For example, processor 120 may include an application specific integrated circuit (ASIC), a digital signal processor (DPS), a digital signal processor (DSP), a programmable logic device (PLS), field-programmable gate array (FPGA), processors, controllers, micro-controller, a microprocessor. Processor 120 may be implemented as a firmware/software module. Such a firmware/software module may be implemented by at least one of software applications written by at least one program languages.

In accordance with at least one embodiment, processor 120 may perform i) operations for obtaining 3D radiograph digital data of a target object and ii) operations for producing a panoramic radiograph using the obtained 3D radiograph digital data. In order to perform such operations, processor 120 may include additional processors. Such configuration of processor 120 will be described with reference to FIG. 2.

Figure 2:
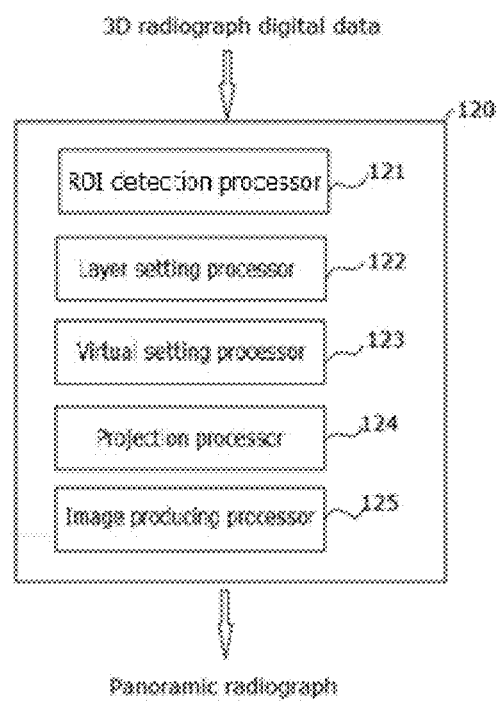
FIG. 2 illustrates a detailed configuration of a processor of a panoramic radiograph producing apparatus in accordance with at least one embodiment.

FIG. 2 illustrates a detailed configuration of a processor of a panoramic radiograph producing apparatus in accordance with at least one embodiment.

Referring to FIG. 2, processor 120 may perform operations for receiving 3D radiograph digital data from 3D CT scanner 20 and perform operations for producing a panoramic radiograph using the received 3D radiograph digital data. Such processor 120 may include ROI detection processor 121, layer setting processor 122, virtual setting processor 123, projection processor 124, and image producing processor 135.

For example, ROI detection processor 121 may perform operation for detecting a region of interest (ROI) from the obtained 3D radiograph digital data. In particular, ROI detection processor 121 may perform operations of i) identifying and isolating ROI 211 including dental arch contour 212 from other regions in the received 3D radiograph, ii) determining voxels associated with identified and isolated ROI 211, and iii) storing the determined voxels in memory 130. Layer setting processor 122 may perform operations for setting at least one image layer in the detected ROI. In particular, layer setting processor 122 may set at least one of virtual image layers within a dental arch in the detected ROI based on predetermined conditions stored in memory 130.

Then, layer setting processor 122 may select one of the virtual image layers and determine information on the selected virtual image layer based on voxels belonging to the virtual image layers.

Virtual setting processor 123 may perform operations for setting a virtual light receiving plane and a virtual light source. In particular, virtual setting processor 123 may i) determine the selected image layer as a focal plane for the target panoramic radiograph to be produced and ii) set virtual locations of a light receiving plane and a light source and distances between the light receiving plane and the light source, between the light receiving plane and the selected image layer, between the light source and the selected image layer.

Projection processor 124 may perform operation for controlling locations of the virtual image receiving plane and the virtual light source to a predetermined position and obtaining a 2D x-ray projection image at the predetermined position. In particular, projection processor 124 may perform operation for i) obtaining all voxels between the virtual light receiving plane and the virtual light source corresponding to each pixel of the light receiving plane and ii) forward projecting the obtained voxels to corresponding pixels of the virtual light receiving plane. Projection processor 124 may perform the similar operations until 2D x-ray projection images of entire dental arch are obtained. Image producing processor 125 may produce a panoramic radiograph of a target dental arch by i) fetching a plurality of 2D x-ray projection images stored in memory 130 and ii) compositing the fetched 2D x-ray projection images together in accordance with at least one embodiment.

As described above, panoramic radiograph producing apparatus 100 may produce a panoramic radiograph using digital data of a 3D radiograph captured and generated by 3D CT scanner 20 in accordance with at least one embodiment. Hereinafter, operations of such panoramic radiograph producing apparatus 100 will be described with reference to FIG. 3 to FIG. 13.

Figure 3:
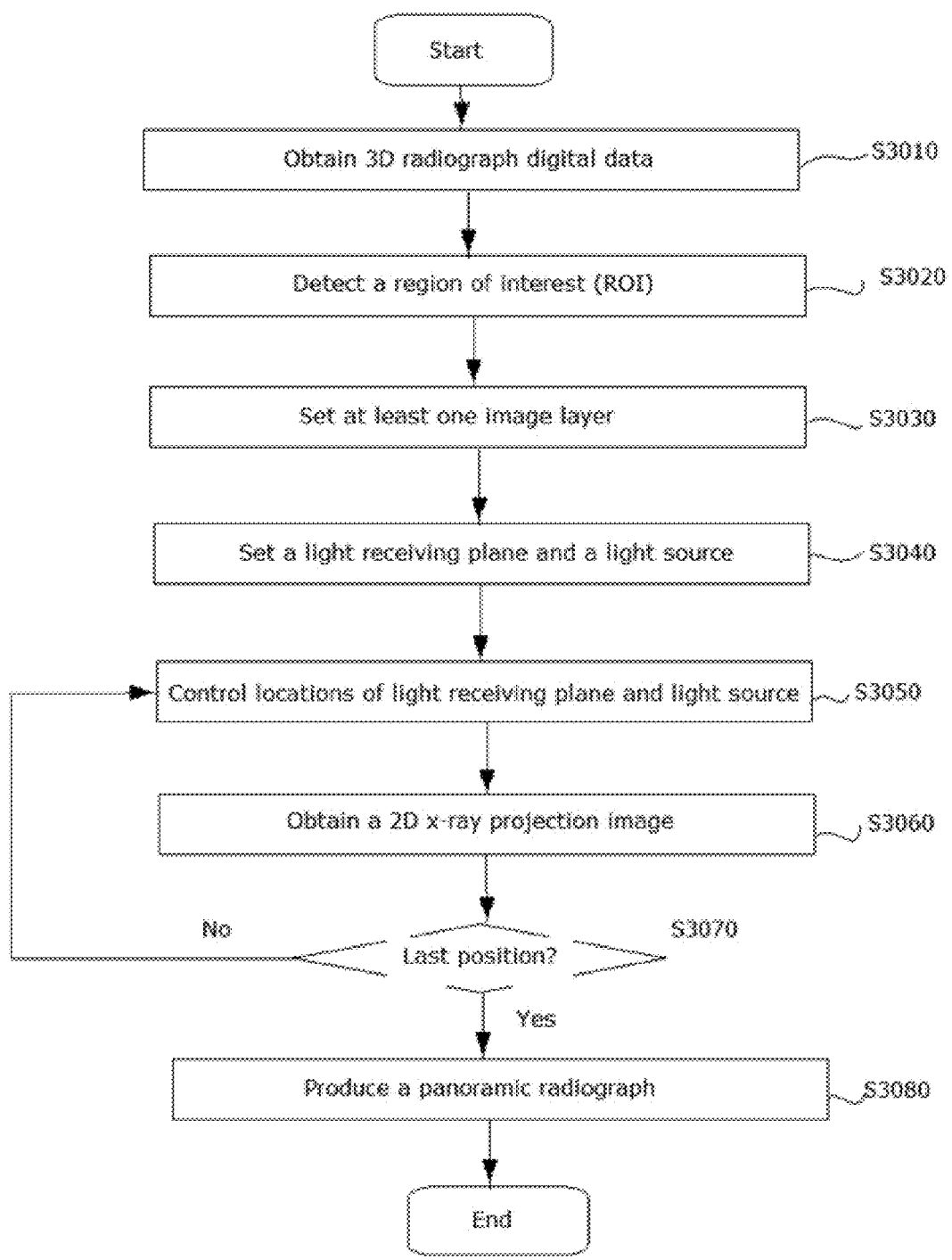
FIG. 3 is a flowchart describing a method for producing a panoramic radiograph using 3D radiograph digital data in accordance with at least one embodiment of the present disclosure.

FIG. 3 is a flowchart describing a method for producing a panoramic radiograph using 3D radiograph digital data in accordance with at least one embodiment of the present disclosure.

Referring to FIG. 3, a 3D radiograph of a target object may be obtained at step S3010. For example, panoramic radiograph producing apparatus 100 obtains 3D radiograph digital data of a patient's dental arch from 3D CT scanner 200. In particular, such 3D radiograph digital data may be received through communication interface 110. The 3D radiograph digital data may be digital data of a 3D radiograph, captured and produced by 3D CT scanner 20. That is, the 3D radiograph digital data may be produced by scanning a patent's head in multiple directions by radiating X-ray and collecting x-ray images formed on a light receiving plane (e.g., x-ray sensor). Such 3D radiograph digital data may be a set of voxel values in order to display the scanned dental arch on display 300 in three dimensions. A voxel is a basic unit of a 3D radiograph, which represents a 3D surface geometry of an object.

That is, panoramic radiograph producing apparatus 100 receives, from 3D CT scanner 20, such 3D radiograph digital data that includes a set of voxel values representing a patient's dental arch in three dimensions. By analyzing and processing such 3D radiograph digital data, various images of a patient's dental arch may be produced and displayed through predetermined display devices.

Figure 4:
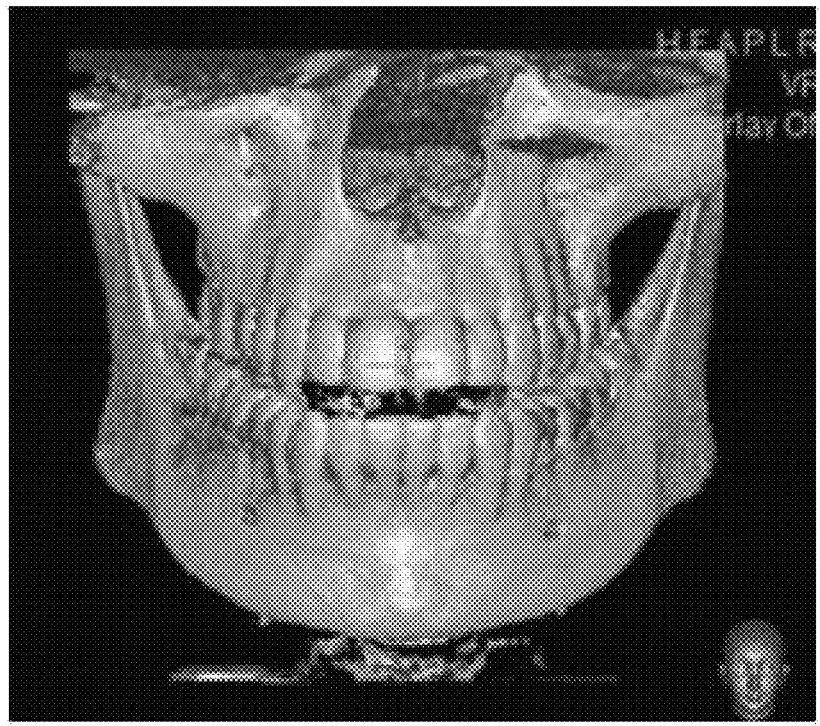
FIG. 4 illustrates 3D radiographs generated by a 3D CT scanner.
Figure 5:
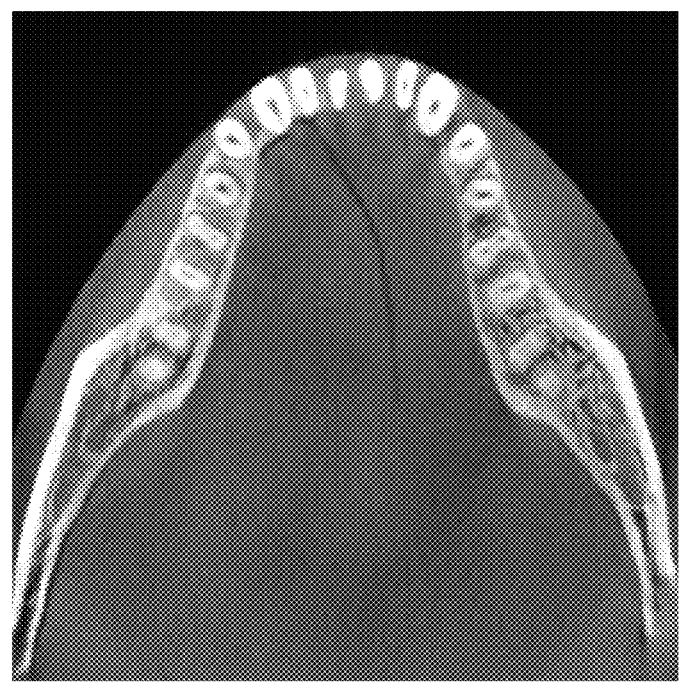
FIG. 5 illustrates one of cross-sectional images included in a 3D radiograph generated by a 3D CT scanner.

For example, FIG. 4 illustrates 3D radiographs generated by 3D CT scanner 20. Referring to FIG. 4, after 3D CT scanner 20 scans a patient's head and produce a 3D radiograph of a dental arch; display 30 may display such a 3D radiograph of the dental arch. As another example, FIG. 5 illustrates one of cross-sectional images (e.g., axial view) included in the 3D radiograph of FIG. 4 generated by 3D CT scanner 200. As described, the 3D radiograph digital data of a target dental arch may be processed to produce various images of the target dental arch in various directions. Such an exemplary cross-section image (e.g., axial view) of FIG. 5 will be used to describe concepts of producing a panoramic radiograph in accordance with at least one embodiment.

As described, panoramic radiograph producing apparatus 100 is described as receiving such 3D radiograph digital data from 3D CT scanner 20, but the embodiments of the present disclosure are not limited thereto. For example, panoramic radiograph producing apparatus 100 may obtain such 3D radiograph digital data through various manners, such as receiving from other entities (e.g., a service server, a personal computer, or another dental equipment located at a remote location) connected through a communication network, receiving from a secondary external memory device (e.g., a USB memory, a portable memory stick, a portable memory bank) coupled directly to panoramic radiograph producing apparatus 100, downloading from a predetermined cloud storage through a communication network or a predetermined webpage, or likes. Furthermore, panoramic radiograph producing apparatus 100 may obtain 3D radiograph digital data produced previously and stored in a predetermined storage device for comparatively long time such as days, months, or yrs.

Figure 6:
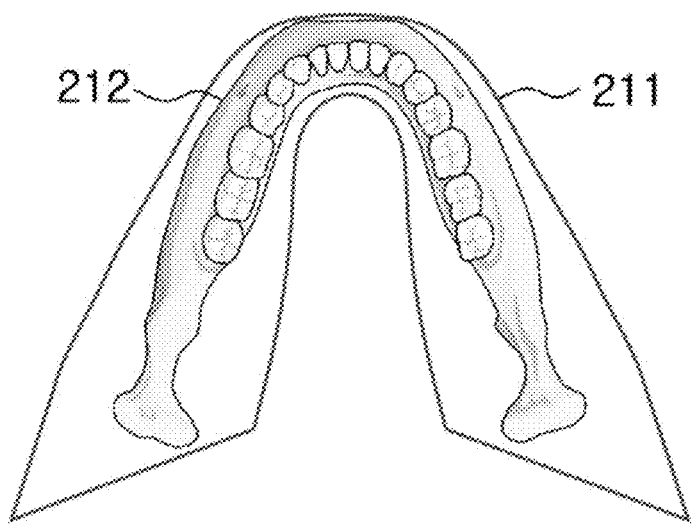
FIG. 6 illustrates a ROI detected in accordance with at least one embodiment.

At step S3020, a region of interest (ROI) may be detected from the obtained 3D radiograph digital data. For example, panoramic radiograph producing apparatus 100 detects a region of interest (ROI) from the 3D radiograph of the target dental arch using a predetermined ROI detection algorithm. In accordance with at least one embodiment, the ROI is only region including a dental arch of a patient in FIG. 5. For example, FIG. 6 illustrates a ROI detected in accordance with at least one embodiment. In particular, ROI detection processor 121 of central processing unit 120 may perform operations based on the predetermined ROI detection algorithm, such as i) identifying and isolating ROI 211 including dental arch contour 212 from other regions in the received 3D radiograph, ii) determining voxels associated with identified and isolated ROI 211, and iii) storing the determined voxels in memory 130.

Such an operation of detecting a ROI may be performed in various manners. For example, ROI detection processor 121 may identify ROI 211 based on conditions and rules previously set before or after the received 3D radiograph has been produced. Alternatively, ROI detection processor 121 may identify ROI 211 based on inputs and selections made by an operator through input/output circuit 140.

In particular, panoramic radiograph producing apparatus 100 may employ a morphology image processing (MIP) algorithm, as a ROI detection algorithm, in accordance with at least one embodiment. In this case, ROI detection processor 121 may i) obtain information on a mask, which was previously stored in memory 130, ii) based on the mask information, identify and isolate a region corresponding to the make from the other regions in the received 3D radiograph, iii) determine voxels associated with the isolated region, and iv) store the determined voxels in memory 130. The mask may be set previously by at least one of a system designer and an operator to include a predetermined region of interest (e.g., dental arch) and stored in memory 130.

The embodiments of the present disclosure are not limited to one particular algorithm to detect a ROI. For example, panoramic radiograph producing apparatus 100 may employ various types of detection algorithms to detect a ROI, such as an edge detection algorithm, a blob detection algorithm, and likes.

For convenience and ease of understanding, FIG. 6 to FIG. 12 illustrate only a ROI including a dental arch of a lower jaw. However, in accordance with at least one embodiment, panoramic radiograph producing apparatus 100 detects a ROI including not only a dental arch of a lower jaw but also a dental arch of an upper jaw and further determines and collects voxels belonging to the ROI including not only a dental arch of a lower jaw but also a dental arch of an upper jaw.

Figure 7:
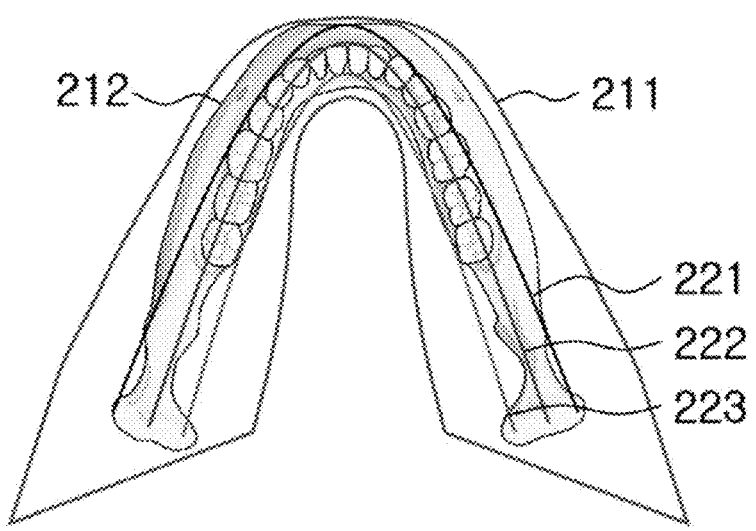
FIG. 7 illustrates three image layers set in a region of interest in accordance with at least one embodiment.

At step S3030, at least one image layers may be set in the detected ROI. For example, FIG. 7 illustrates three image layers set in a region of interest in accordance with at least one embodiment. As shown in FIG. 7, panoramic radiograph producing apparatus 100 sets three image layers 221, 222, and 223 in the detected ROI 211. Such three image layers 221, 222, and 223 are also trajectories of rotating a virtual light source and a virtual light receiving plane. That is, three image layers 221, 222, and 223 may be focal planes of a target panoramic radiograph to be produced and curved surfaces inside the 3D dental arch image 212.

In particular, image layer setting processor 122 of central processing unit 120 may set at least one of virtual image layers 221, 222, and 223 within the dental arch 212 in the detected ROI 211 based on predetermined conditions stored in memory 130. Then, image layer setting processor 122 may select one of the virtual image layers 221, 222, and 223 and determine information on the selected virtual image layer based on voxels belonging to the virtual image layers 221, 222, and 223. After setting three image layers 221, 222, and 223, and selecting one of three image layers 221, 222, and 223 as a focal plane, corresponding information (e.g., voxel) of image layers 221, 222, 223, and selected image layer may be stored in memory 130.

At step S3040, a light receiving plane and a light source may be virtual set. For example, panoramic radiograph producing apparatus 100 may virtually set a light receiving plane and a light source in accordance with at least one embodiment. Such a light receiving plane may be a virtual x-ray sensor that receives x-ray projected from the light source through a patient's head. On the light receiving plane, a 2D x-ray projection image may be formed. Such a 2D x-ray projection image may be obtained at each of predetermined positions and multiple 2D x-ray projection images are combined to produce a panoramic radiograph. Such operation will be described in more detail. The light source may denote a virtual x-ray source that radiates an x-ray toward a patient' head and the x-ray sensor. Light receiving plane 231 may include a predetermined height and width and have a plurality of virtual pixels for forming a 2D x-ray projection image thereon.

Figure 8:
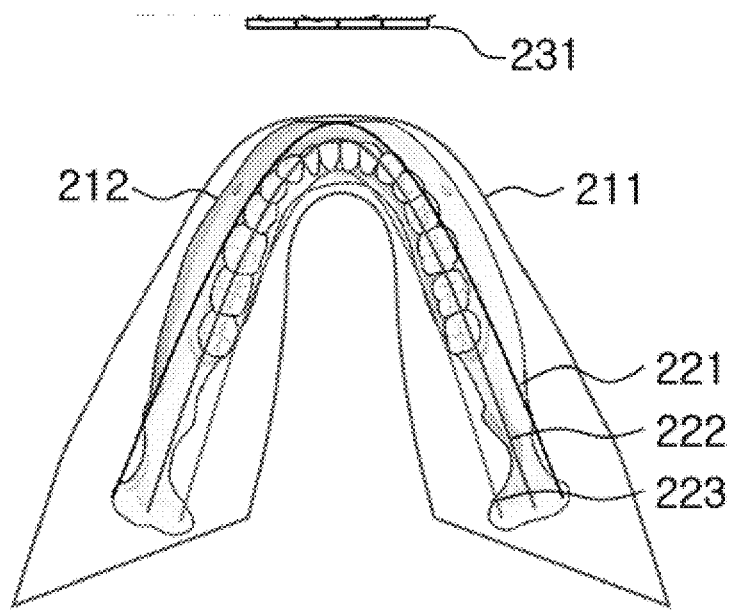
FIG. 8 illustrates a light receiving plane and a light source, virtually set with a dental arch in accordance with at least one embodiment.

For example, FIG. 8 illustrates a light receiving plane and a light source, virtually set with a dental arch in accordance with at least one embodiment. As shown in FIG. 8, virtual setting processor 123 of central processing unit 120 may i) determine the selected image layer (e.g., one of 221, 222, and 223) as a focal plane for the target panoramic radiograph to be produced and ii) set virtual locations of light receiving plane 231 and light source 232 and distances between light receiving plane 231 and light source 232, between light receiving plane 231 and the selected image layer, between light source 232 and the selected image layer.

As shown in FIG. 8, virtual setting processor 123 may locate virtual light receiving plane 231 to face virtual light source 232 with image layers 221 to 223 interposed therebetween. Furthermore, virtual setting processor 123 may locate virtual light receiving plane 231 in front of dental arch 212 and locate virtual light source 232 in back of dental arch 212. In addition, virtual setting processor 123 may locate a focal plane at one of image layers 221, 222, and 223 in accordance with at least one embodiment. That is, virtual setting processor 123 may determine locations of virtual light receiving plane 231 and virtual light source 232 as described above and store information on the locations in memory 130.

Figure 9:
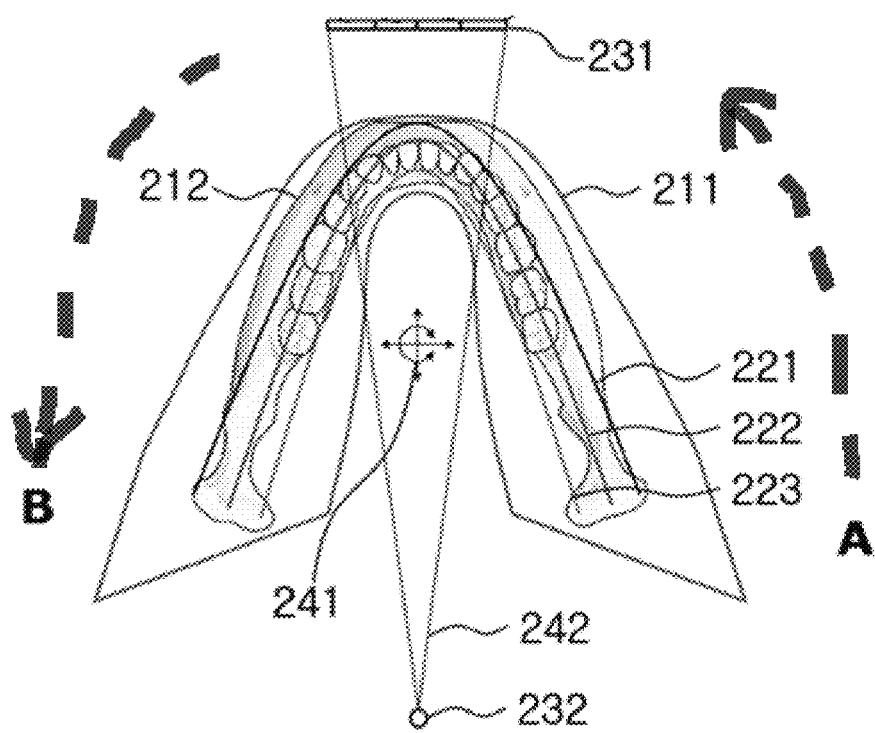
FIG. 9 illustrates a virtual light receiving plane and a virtual light source positioned to obtain a 2D x-ray projection image of a certain part of a dental arch.

At step S3050, locations of the virtual image receiving plane and the virtual light source may be controlled to a predetermined position. For example, panoramic radiograph producing apparatus 100 may adjust locations of virtual image receiving plane 231 and virtual light source 232 to virtually radiate an x-ray to a predetermined region of dental arch 212 in order to obtain a 2D x-ray projection image of the predetermined region. Accordingly, virtual setting processor 123 moves virtual image receiving plane 231 and virtual light sources 232 to a predetermined position (e.g., projection start position A) by rotating virtual image receiving plane 231 and virtual light source 232 on virtual center point 241, as shown in FIG. 9. For example, FIG. 9 illustrates a virtual light receiving plane and a virtual light source positioned to obtain a 2D x-ray projection image of a certain part of a dental arch. At an initial stage, projection processor 124 of central processing unit 120 may move virtual image receiving plane 231 and virtual light source 232 to the projection start position A by rotating virtual image receiving plane 231 and virtual light source 232 on virtual center point 241.

At step S3060, a 2D x-ray projection image of a predetermined position may be obtained. For example, panoramic radiograph producing apparatus 100 may obtain a 2D x-ray projection image of a predetermined position by calculating pixel values of virtual light receiving plane 231 using voxels that are located between light source 232 and light receiving plane 231 and are corresponding to each of pixels of virtual light receiving plane 231.

Figure 10:
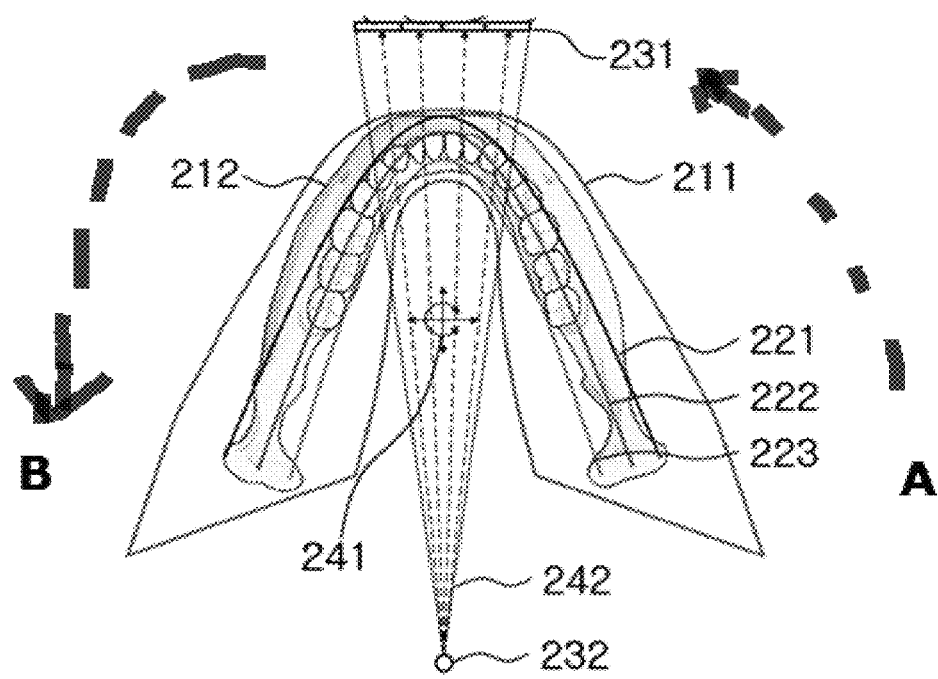
FIG. 10 is a diagram for describing an operation for obtaining a 2D x-ray projection image formed on a virtual light receiving plane in accordance with at least one embodiment.

For example, FIG. 10 is a diagram for describing an operation for obtaining a 2D x-ray projection image formed on a virtual light receiving plane in accordance with at least one embodiment. As shown in FIG. 10, in order to obtain a 2D x-ray projection image formed on virtual light receiving plane 231 at the controlled position, panoramic radiograph producing apparatus 100 may i) obtain all voxels between virtual light receiving plane 231 and virtual light source 232 corresponding to each pixel of light receiving plane 231 and ii) forward projecting the obtained voxels to corresponding pixels of virtual light receiving plane 231. As shown in FIG. 10, the obtained voxels may be voxels belonging in region 242 (e.g., between virtual light source 232 and virtual light receiving plane 231).

In particular, projection processor 124 may i) determine corresponding voxels between each pixel of light receiving plane 231 and virtual light source 232, ii) calculating a value of each pixel by performing forward-projection on the corresponding voxels, and iii) storing the calculated pixel values as the 2D x-ray projection image of a current position.

Such forward projection may be curvilinear (line) integral. That is, each pixel value of the 2D x-ray projection image virtually formed on virtual light receiving plane 231 may be calculated by performing line integral on all voxel values between each pixel of virtual light receiving plane 231 and virtual light source 323. In particular, projection processor 124 may perform line integral with corresponding voxels to calculate each pixel value of virtual light receiving plane 231. After calculating all of pixel values, Projection processor 124 may store the calculated pixel values in memory 130 as a 2D x-ray projection image of a current position.

At step S3070, determination may be made so as whether a current position is a projection end position B (e.g., Last Position). For example, projection processor 124 determines whether the controller position of light receiving plane 231 and light source 232 is the projection end position B.

When the current position is not the projection end point B (No—S3070), locations of the virtual image receiving plane and the virtual light source may be controlled to the next position at step S3050 and another 2D x-ray projection image of the next position may be obtained at step S3060.

Figure 11:
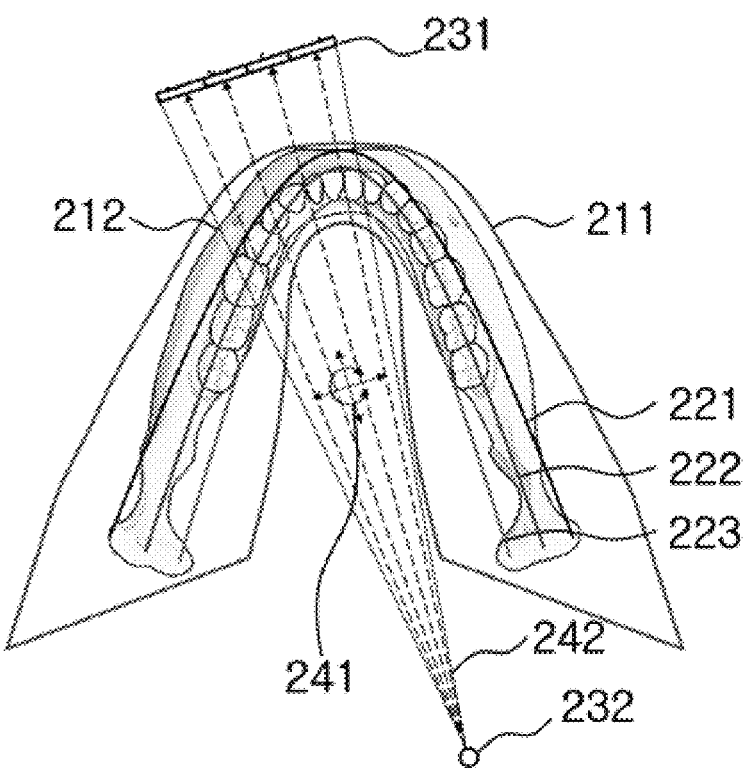
FIG. 11 is a diagram for describing an operation for rotating a virtual light receiving plane and a virtual light source in a predetermined distance to a next position and obtaining a 2D x-ray projection image formed on a virtual light receiving plane at the next position in accordance with at least one embodiment.

For example, FIG. 11 is a diagram for describing an operation for rotating a virtual light receiving plane and a virtual light source in a predetermined distance to a next position and obtaining a 2D x-ray projection image formed on a virtual light receiving plane at the next position in accordance with at least one embodiment. As shown in FIG. 11, panoramic radiograph producing apparatus 100 may move locations of virtual image receiving plane 231 and virtual light source 232 to the next position by rotating virtual image receiving plane 231 and virtual light source 232 on virtual center point 241 to a predetermined distance. Such a rotation distance may be previously set and stored in memory 130. After obtaining a 2D x-ray projection image of a current position, panoramic radiograph producing apparatus 100 may repeatedly rotate virtual light receiving plane 231 and light source 232 on center point 241 in the predetermined rotation distance until the current position reaches the last position (e.g., projection end position B).

After moving to the next position, panoramic radiograph producing apparatus 100 may obtain a 2D x-ray projection image of the next position by calculating pixel values of virtual light receiving plane 231 using voxels that are located between light source 232 and light receiving plane 231 and are corresponding to each of pixels of virtual light receiving plane 231. As described, in order to obtain a 2D x-ray projection image formed on virtual light receiving plane 231 at the next position, panoramic radiograph producing apparatus 100 may i) obtain all voxels between virtual light receiving plane 231 and virtual light source 232 corresponding to each pixel of light receiving plane 231 and ii) forward projecting the obtained voxels to corresponding pixels of virtual light receiving plane 231. As shown in FIG. 11, the obtained voxels may be voxels belonging in region 242 (e.g., between virtual light source 232 and virtual light receiving plane 231). After calculating all of pixel values, panoramic radiograph producing apparatus 100 may store the calculated pixel values in memory 130 as a 2D x-ray projection image of the next position. Such operation of the step S3060 may be repeatedly performed until a currently position reaches the last position (e.g., projection end position B). By repeatedly performing such operation, panoramic radiograph producing apparatus 100 may obtain a plurality of 2D x-ray projection images of entire dental arch 212.

Referring back to FIG. 3, when the current position is the projection end point B (Yes—S3070), a panoramic radiograph may be produced at step S3080. For example, image producing processor 125 may produce a panoramic radiograph of a target dental arch by i) fetching a plurality of 2D x-ray projection images stored in memory 130 and ii) compositing the fetched 2D x-ray projection images together in accordance with at least one embodiment.

Figure 12:
FIG. 12 illustrates exemplary 2D x-ray projection images in accordance with at least one embodiment.

For example, FIG. 12 illustrates exemplary 2D x-ray projection images in accordance with at least one embodiment. Such 2D x-ray projection images may be properly overlapped and combined together to produce a panoramic radiograph of FIG. 13. In at least one embodiment, a shift and adding operation may be used to produce a panoramic radiograph. For example, the panoramic radiograph may be produced by (a) scaling sizes of images reconstructed with an image layer or images to be used for a reconstruction in consideration of a size of a predetermined reference image according to a reference image layer; (b) selecting an image in part or full representing a predetermined region of interest clearly among scaled images; and (c) providing a panoramic image with selected image. Such operations are disclosed in U.S. patent application Ser. No. 14/401,726, the teachings of which are incorporated herein their entirety by reference.

Figure 13:
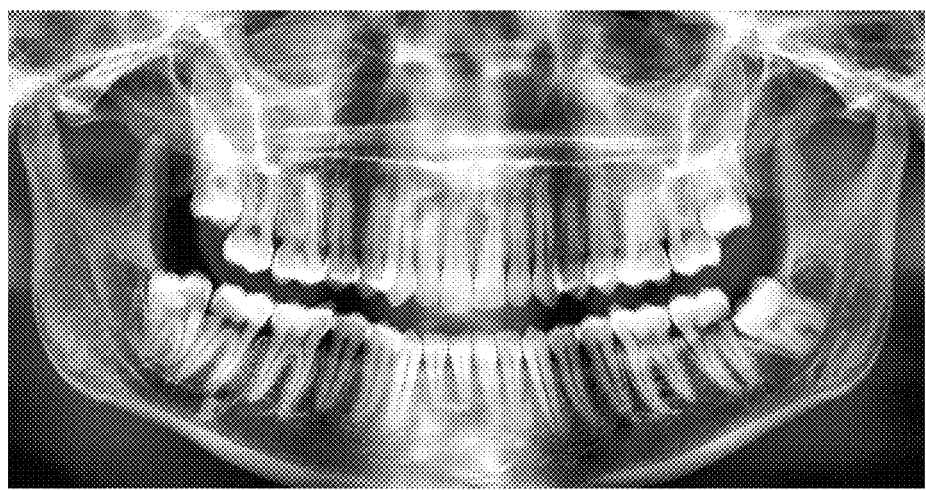
FIG. 13 illustrates a panoramic radiograph produced using 3D radiograph digital data in accordance with at least one embodiment.

For example, FIG. 13 illustrates a panoramic radiograph produced using 3D radiograph digital data in accordance with at least one embodiment. As shown in FIG. 13, although the panoramic radiograph is produced without using a panoramic radiography machine, the produced panoramic radiograph is very similar to that photographed by the panoramic radiography machine. In particular, the produced panoramic radiograph of FIG. 13 has a projected image of a cervical vertebral of a patient, which is very similar to a panoramic radiograph taken by the typical panoramic radiography machine.

After producing the panoramic radiograph of FIG. 13, panoramic radiograph producing apparatus 100 may transmit the produced panoramic radiograph to display 30 or stored in memory 130.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Moreover, the terms "system," "component," "module," "interface,", "model" or the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

The present invention can be embodied in the form of methods and apparatuses for practicing those methods. The present invention can also be embodied in the form of program code embodied in tangible media, non-transitory media, such as magnetic recording media, optical recording media, solid state memory, floppy diskettes, CD-ROMs, hard drives, or any other machine-readable storage medium, wherein, when the program code is loaded into and executed by a machine, such as a computer, the machine becomes an apparatus for practicing the invention. The present invention can also be embodied in the form of program code, for example, whether stored in a storage medium, loaded into and/or executed by a machine, or transmitted over some transmission medium or carrier, such as over electrical wiring or cabling, through fiber optics, or via electromagnetic radiation, wherein, when the program code is loaded into and executed by a machine, such as a computer, the machine becomes an apparatus for practicing the invention. When implemented on a general-purpose processor, the program code segments combine with the processor to provide a unique device that operates analogously to specific logic circuits. The present invention can also be embodied in the form of a bitstream or other sequence of signal values electrically or optically transmitted through a medium, stored magnetic-field variations in a magnetic recording medium, etc., generated using a method and/or an apparatus of the present invention.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

As used herein in reference to an element and a standard, the term "compatible" means that the element communicates with other elements in a manner wholly or partially specified by the standard, and would be recognized by other elements as sufficiently capable of communicating with the other elements in the manner specified by the standard. The compatible element does not need to operate internally in a manner specified by the standard.

No claim element herein is to be construed under the provisions of 35 U.S.C. § 112, sixth paragraph, unless the element is expressly recited using the phrase "means for" or "step for."

Although embodiments of the present invention have been described herein, it should be understood that the foregoing embodiments and advantages are merely examples and are not to be construed as limiting the present invention or the scope of the claims. Numerous other modifications and embodiments can be devised by those skilled in the art that will fall within the spirit and scope of the principles of this disclosure, and the present teaching can also be readily applied to other types of apparatuses. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An apparatus of producing a panoramic radiograph of a target object using a three dimensional (3D) radiograph of the same object, the apparatus comprising:
    a communication circuit configured to receive 3D radiograph digital data of the 3D radiograph; and
    a processor configured to:
        generate a plurality of x-ray projection images of the target object by performing forward-projection on voxels associated with the target object, and
        combine the generated x-ray projection images to produce the panoramic radiograph of the target object,
    wherein the processor is configured to:
    detect a region of interest (ROI) including the target object in the 3D radiograph based on the received 3D radiograph digital data;
    virtually locate a light receiving plane in front of the detected ROI and virtually locate a light source in back of the detected ROI;
    determine voxels between the light source and each pixel of the light receiving plane; and
    performing line integral on the determined voxels to generate the plurality of x-ray projection images.

2. The apparatus of claim 1, wherein the processor is configured to:
    use at least one of a morphology image processing (MIP) algorithm, an edge detection algorithm, and a blob detection algorithm to detect the ROI; and
    set at least one image layer in the detected ROI.

3. The apparatus of claim 2, wherein the processor is configured to:
    rotate the light receiving plane and the light source along the at least one image layer to generate the plurality of x-ray projection images.

4. An apparatus of producing a panoramic radiograph of a target object using a three dimensional (3D) radiograph of the same object, the apparatus comprising:
    a communication circuit configured to receive 3D radiograph digital data of the 3D radiograph; and
    a processor configured to:
        generate a plurality of x-ray projection images of the target object by performing forward-projection on voxels associated with the target object, and
        combine the generated x-ray projection images to produce the panoramic radiograph of the target object,
    wherein the processor is configured to perform the forward-projection by:
        virtually locating a light receiving plane in front of a region of interest (ROI) and virtually locating a light source in back of the ROI; and
        determining voxels between the light source and each pixel of the light receiving plane and performing line integral on the determined voxels,
    wherein the 3D radiograph of the same object is generated by a 3D computerized tomography (CT) scanner which is separated from the apparatus.

5. A method of producing a panoramic radiograph of a target object using a three dimensional (3D) radiograph of the same object, the method comprising:
    receiving 3D radiograph digital data of the 3D radiograph;
    generating a plurality of x-ray projection images of the target object by performing forward-projection on voxels associated with the target object based on the received 3D radiograph digital data; and combining the generated x-ray projection images to produce the panoramic radiograph of the target object, wherein the generating comprises:

detecting a region of interest (ROI) including the target object in the 3D radiograph based on the received 3D radiograph digital data;

virtually locating a light receiving plane in front of the detected ROI and virtually locating a light source in back of the detected ROI;

determining voxels between the light source and each pixel of the light receiving plane; and generating the plurality of x-ray projection images by performing line integral on the determined voxels.

6. The method of claim 5, wherein the detecting comprising:

using at least one of a morphology image processing (MIP) algorithm, an edge detection algorithm, and a blob detection algorithm to detect the ROI; and setting at least one image layer in the detected ROI.

7. The method of claim 5, wherein the detecting comprising:

rotating the light receiving plane and the light source along the at least one image layer at a predetermined distance to generate the plurality of x-ray projection images.

8. The method of claim 5, wherein the 3D radiograph of the same object is generated by a 3D computerized tomography (CT) scanner separated from the apparatus.

* * * * *